(12) United States Patent
Fotinos

(10) Patent No.: US 6,335,388 B1
(45) Date of Patent: Jan. 1, 2002

(54) PROLAMINE-PLANT POLAR LIPID COMPOSITION, ITS METHOD OF PREPARATION AND APPLICATIONS THEREOF

(75) Inventor: Spiros Fotinos, Athens (GR)

(73) Assignee: Lavipharm Laboratories Inc., East Windsor, NJ (US)

( * ) Notice: Subject to any disclaimer, the term of this patent is extended or adjusted under 35 U.S.C. 154(b) by 0 days.

(21) Appl. No.: 09/165,846

(22) Filed: Oct. 2, 1998

Related U.S. Application Data

(60) Provisional application No. 60/060,897, filed on Oct. 3, 1997.

(51) Int. Cl.[7] .......................... C08L 89/00; A61K 9/70; A61K 9/127
(52) U.S. Cl. .......................... 524/20; 524/17; 523/105; 424/78.02; 424/78.06; 424/443; 424/450; 514/2; 514/21
(58) Field of Search .......................... 523/105; 524/17, 524/20, 21; 424/78.02, 78.06, 443, 450; 514/2

(56) References Cited

U.S. PATENT DOCUMENTS

| | | |
|---|---|---|
| 4,137,300 A | 1/1979 | Sheth et al. |
| 4,394,373 A | 7/1983 | Malette et al. |
| 5,160,742 A | 11/1992 | Mazer et al. |
| 5,182,130 A | 1/1993 | Haralampu et al. |
| 5,201,745 A | 4/1993 | Tayot et al. |
| 5,641,814 A | 6/1997 | Martin |
| 6,045,809 A * | 4/2000 | Postaire et al. ............. 424/400 |
| 6,056,944 A * | 5/2000 | Finidori |

FOREIGN PATENT DOCUMENTS

| | | |
|---|---|---|
| EP | 0090559 A2 | 10/1983 |
| EP | 0187703 A2 | 7/1986 |
| EP | 0486294 A2 | 5/1992 |
| EP | 0518697 A2 | 12/1992 |
| EP | 0621044 A2 | 10/1994 |
| WO | WO93/10731 | 6/1993 |
| WO | WO93/12771 | 7/1993 |
| WO | WO95/28964 | 11/1995 |
| WO | WO96/37912 | 11/1996 |

OTHER PUBLICATIONS

Stella, V., et al. (1995); "Gliadin Films. I: Preparation and in vitro evaluation as a carrier for controlled drug release" *International Journal of Pharmaceutics* 121 (1995) 117–121.

Thacharodi, D. and Panduranga Rao, K. (1995); "Development and in vitro evaluation of chitosan-based transdermal drug delivery systems for the controlled delivery of propranolol hydrochloride" *Biomaterials* 1995, vol. 16 No. 2 145–148.

* cited by examiner

Primary Examiner—Peter Szekely
(74) Attorney, Agent, or Firm—Dechert; Thomas S. Deibert

(57) ABSTRACT

Prolamine-plant polar lipid compositions are provided, said compositions including a mixture of a prolamine, a plant polar lipid, at least one polyalcohol in a hydro-alcoholic solution, and an active agent, wherein the composition forms a substantially homogeneous dispersion with skin adhesive properties; wherein the dispersion forms a film and wherein the film contains a gradient of concentrations of the active agent.

22 Claims, 4 Drawing Sheets

PROLAMINE-PLANT POLAR LIPID COMPOSITION, ITS METHOD OF PREPARATION AND APPLICATIONS THEREOF

CROSS REFERENCE

This invention claims priority from provisional application Ser. No. 60/060,897 filed Oct. 3, 1997, the provisional application being here incorporated by reference.

TECHNICAL DESCRIPTION

This invention is directed to a prolamine-plant polar lipid composition, its method of preparation and its uses for delivery of active agents, including therapeutic agents and cosmetic agents, and for wound healing, wound protection and hemostasis.

BACKGROUND TO THE INVENTION

A number of different approaches are available for delivering active agents to a predetermined target site in the body. For example, formulations have been developed for systemic delivery of therapeutic agents which are provided orally and are degraded in the buccal cavity or in the bowel so as to release a therapeutic agent in a controlled manner. Alternatively, systemic delivery of therapeutic agents has been achieved by transdermal delivery using multilayered patches Patches have been designed for use in transdermal delivery or topical delivery of drugs and have also been used as wound dressings in which the presence of a therapeutic agent is optional.

Developments in formulations suitable for ingestion include polymeric coatings that slowly degrade and liberate drug over an extended period of time. Polymeric coatings may be formed from protein or carbohydrates or lipids. Examples of proteins include albumin (Ohya et al. J. Macromol. Sci. Chem. 28, (1991), 743–760); gelatin (Yan et al., Biomaterials 12, (1991), 640–644); cross linked gelatin (Digenis et al. J. Pharm. Sci. 83, (1994), 915–921); gliadin (Stella et al. International Journal of Pharmaceutics 121, (1995), 117–121; WO 96/21462; U.S. Pat. No. 5,160,732); and casein (Jayakrishnan et al. Int. J. Pharm., 106, (1994), 221–228). Examples of polysaccharides include cellulose derivatives (Ghorab et al. J. Microencapsul. 7, (1990), 447–454); and examples of lipids include ceramide (WO 96/21462). Ceramides have been used as coatings for granules, tablets, and nutritives U.S. Pat. Nos. 4,137,300, 5,160,742, 5,182,130, EP-A-O 090 559, WO-A-96/21462 and WO-A-93/12771. For example, in U.S. Pat. No. 5,160,742; the active ingredient is an antibiotic which is contained in a core and has at least one coating of prolamine and one coating of an enteric compound. Similarly, in U.S. Pat. No. 5,182,130, edible coatings are described that are formed from prolamines that are applied to an active agent contained in an aqueous microparticle. Gliadins have also been used to form capsules to deliver drugs orally. Stella et al. (1995) reported an oral drug delivery capsules in which the active agent, paracetemol, was incorporated into a capsule formed from gliadin. Stella also incorporated paracetemol in a gliadin containing chewing gum for delivery by means of mastication. Despite innovations in oral drug delivery, there exists a need for improvements in controlled release of therapeutic agents at a sustained rate over extended periods of time.

Whereas tablets and capsules are suitable only for delivery of a therapeutic agent systemically through the stomach or intestinal mucosa, transdermal delivery, which relies on the adhesion to the skin of the patch, offers a potentially more direct route of delivery to the blood. Advantages of transdermal delivery include: avoidance of first pass effects described for tablets and capsules; and problems associated with stomach irritation. In certain circumstances, it is desirable to deliver a therapeutic agent or cosmetic agent topically to the skin at a target site. Both transdermal and topical delivery devices rely on the adherence of a patch to the surface of the skin or other body surface such as the surface of nose, mouth, vagina, or rectum or wound surface.

Patch delivery devices are generally either of the drug reservoir type or alternatively contain the active agent dispersed throughout a polymer matrix. Where polymer matrices are utilized, these are generally synthetic polymers such as acrylates. However, a naturally occurring polycationic polysaccharide polymer, identified as chitosan, has been used in sustained release formulations of therapeutic agents (Thacharodi and Rao; Biomaterials 16 (1995) 145–148). Chitosan is difficult to purify and is commonly contaminated with proteins. In addition, chitosan lacks adhesive properties. Therefore, an adhesive layer formed from acrylates is laminated to the chitosan to form the interface between the body and the patch. However, the use of chitosan may be associated with adverse skin reactions. Another naturally occurring polymer that has been used in patches is protein. For example, animal collagen is a protein which has been used as an adhesive polymer. Just as with chitosan, a separate adhesive layer is recommended for the collagen laminate. (EP 0 518697A2).

Collagen has been used in wound healing applications to form pads for purposes of controlling bleeding (WO 93/10731). The collagen pads absorb wound exudate to produce a firm primary vital adhesion to the wound. EP 0 621 044 A2 reports an attempt to increase the strength of collagen sheets to avoid tearing when wet and further suggests the introduction of agents into the collagen to assist the healing process. Problems associated with the use of collagen, a biological polymer from animals, include those arising from the fact that collagen is an animal protein. These problems include possible contamination of the protein with disease-causing viruses; and stimulation of an immune response in the immunological active environment of a wound during multi-day exposure of the collagen film to the wound.

There are a number of limitations associated with existing patches. These include: irritation of the body surface associated with the patch; reversible adhesive attachment of the patch to the body surface for extended periods of time; and capacity for retaining active agents. In certain situations, it is desirable for the patch to have a large surface area such as in wound healing applications in which case, the plasticity of the patch and the lack of irritation are important desirable characteristics. There is an unmet need for biocompatible adhesive polymers for transdermal or topical delivery of drugs to body surfaces as well as for patches suitable for wound healing and hemostasis, that cause minimal irritability, have a suitable drug capacity to modulate the size of the patch, are not immunogenic and are free from contamination with pathogens. Furthermore, there is an unmet need for a moisturizing anti-irritant adhesive non-animal protein film that is biodegradable, and has the plasticity to remain intact in a moist environment. In addition, it would be desirable to obtain a film which may be suitable for wound protection and healing so as to seal moisture into a healing wound while excluding infectious agents from the air and permitting diffusion of oxygen to the wound.

SUMMARY OF THE INVENTION

The invention addresses the unmet need for a biocompatible adhesive polymer for transdermal or topical delivery of drugs to body surfaces as well as for patches suitable for wound healing and hemostasis, that cause minimal irritability, have reduced immunogenicity, and are substantially free from contamination with pathogens. Furthermore, the invention provides a film that seals moisture into a healing wound while excluding infectious agents from the air and permitting diffusion of oxygen to the wound.

In an embodiment of the invention, a composition is provided that includes a mixture of a prolamine, a plant polar lipid and at least one polyalcohol in a hydro-alcoholic solution so as to form a substantially homogeneous dispersion with skin adhesive properties. In a preferred embodiment, the prolamine is a cereal prolamine more particularly a gliadin having a w/w concentration of 20–40% where the plant polar lipid is isolated from a cereal and includes at least one of a ceramide or a glycosylceramide at a concentration greater than 50%, and a w/w concentration of 0.1%–5%, the prolamine and plant polar lipid being homogeneously dispersed in a hydro-alcoholic solution.

In an embodiment of the invention, the dispersion forms a film, where the film may be rolled into a compact form so as to be capable of insertion within a capsule. The film may include a plasticizing agent such polyalcohol for example, glycerol or sorbitol where the concentration of the polyalcohol may be as much as 80% w/w (dry weight).

In an embodiment of the invention, an active agent is contained within the prolamine-plant polar lipid-polyalcohol dispersion where the active agent may be a therapeutic agent or a cosmetic agent for topical or systemic delivery. The method may direct the active agent to the target site via oral, buccal, rectal, vaginal or topical routes. The homogeneous dispersion may be aerosolized, the aerosol capable of forming a film on the body surface.

In an additional embodiment of the invention, a method for forming a gel is provided that includes the steps of selecting a prolamine and a plant polar lipid; and mixing the prolamine and the plant polar lipid at an effective temperature and for an effective time in a hydroalcohol solvent so as to form a substantially homogeneous dispersion, the dispersion forming a gel. In preferred embodiments, the effective temperature is in the range of 40–50° C. and the time is least 10 minutes In an embodiment of the invention, a method is provided for delivering an active agent to a target site, that includes forming a homogeneous dispersion of a prolamine, a plant polar lipid and at least one polyalcohol in a hydro-alcoholic solution; adding at least one active agent to the dispersion; permitting the dispersion to form a skin adhesive gel; and applying the gel to the skin so as to deliver the active agent to the target site. In further embodiments, the target site may be systemic or topical and the active agent selected from the group comprising: local and systemic pain relievers, antiarthritis agents; buccally active agents, agents for enhancing dental hygiene, agents for enhancing mouth hygiene, antimicrobials agents, anesthetic agents, keratolytic agent; wound healing agents; antipyretics; anti-inflammatory agents, antispasmodics, sympathomimetic drugs, antiparasitic agents, hypoglycemic drugs, nutritional agents, cardiovascular agents, agents for smoking cessation, vitamins, hemostatic agents, skin growth agents. The active agent may further be selected from the group comprising: agents for improving skin appearance, topically active agents for treating dermal and nail diseases; anti-hyperpigmentation, anti-blotching, anti-aging, eye contour, slimming, anti-cellulite, soothing/sunburn anti-irritating, skin firming and lifting, anti-elastase and anti-collagenase agents, free radical scavengers, seboregulators, hydratives, and AHA (α-hydroxy acids) specific products.

A further embodiment of the invention is a method for protecting a wound, that includes the steps of forming a homogeneous dispersion of a prolamine, a plant polar lipid and at least one polyalcohol in a hydro-alcoholic solution; permitting the dispersion to form a skin adhesive gel; and applying the gel to the skin so as to provide protection to the wound. The method may further include adding an oxidizing agent to the dispersion where the oxidising agent may be vitamin E.

DETAILED DESCRIPTION OF THE INVENTION

Figure 1:
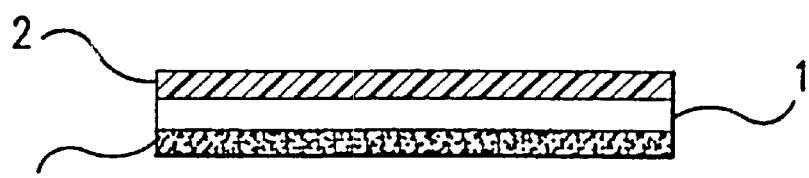
FIG. 1 shows a three layered patch with a polymeric matrix layer (1) between a backing layer (2) and a release liner (3).

A novel adhesive polymer is provided that, in a preferred embodiment, is formed from a dispersion that includes prolamines and polar lipids of plant origin.

The composition may be used as a dosage unit for holding an effective amount of an active substance and for delivering the active substances systemically or locally. The dosage unit may be in the form of a patch or film for dermal (topical), transdermal, mucosal, or buccal administration and also for wound healing, wound protection and hemostasis. The composition may also be administered on a wound so as to form a protective film in the absence of therapeutic agents so as to promote wound healing. Active substances may be incorporated into the film for targeting to a systemic or local site so as to further promote healing. The size and shape of the composition or dosage unit may be designed to fit the site of application.

The term "active substances" as used here and in the claims includes any therapeutic or cosmetic agent.

The term "therapeutic agent" as used here and in the claims includes any inorganic or organic compound having hydrophilic or hydrophobic properties or both, known in the art to be used for the treatment of certain disorders.

The term "cosmetic agent" as used herein, includes any compound known in the art to be used for improving skin appearance.

The term "film" as defined here and in the claims is a composition formed from a dispersion of polar lipids and proteins in a substantially homogeneous dispersion, wherein the composition occupies a three dimensional volume in which one dimension is significantly smaller than the other two dimensions. The film may be precast or formed in situ (at the target site).

The term "patch" is defined here and in the claims as a precast laminate that includes at least 3 layers, a backing layer, a polymer layer and a release liner.

The term "selected site" is defined here and in the claims as any part of the surface of the subject's body including surfaces in the nose, mouth, gut, vagina and rectum.

The terms "systemically" is defined here and in the claims as the mode of administration of the active substances such that the active substance is targeted to the systemic circulation The terms "topically" is defined here and in the claims as the mode of administration of the active substances such that the active substance is targeted superficially to a selected site.

The term "stable" is defined here and in the claims as maintaining the functional properties of the composition before the expiration of a predetermined time without significant chemical changes.

The term "safe" as used herein, means that no significantly undesirable effects are induced upon the application of the composition.

The novel composition of the invention is a homogeneous dispersion of prolamines and plant polar lipids to form a biocompatible adhesive polymer. In a preferred embodiment, the prolamine is a plant prolamine and is more preferably a cereal prolamine. In particular, Examples 1–13 utilize the naturally occurring wheat prolamine identified as gliadin. However, plant prolamines derived from alternate cereals may be used such as zein from corn and hordein from barley. Examples 1–13 utilize gliadins from commercial sources. Alternatively, gliadins may be manufactured according to FR 9311667. According to the invention, any gliadin may be used including any selected chemical form of gliadin as obtained during purification. Alternatively, a mixture of different types of gliadins may be used.

Prolamines are characterized by being rich in glutamine and proline, and low in basic amino acids and show a high degree of sequence homology between different subtypes. The prolamines are hydrophobic and lipid-binding as well as being capable of interacting with hydrophilic molecules. They are soluble in hydro-alcoholic solutions (50–60% n-propanol or 60–90% ethanol) to form a viscous gel having adhesive properties. This gel can be processed to form a film. Moreover, dry gliadin film restores its adhesive properties upon hydration.

Polar lipids may include glycolipids, phospholipids, and sphingolipids collectively known as ceramides. Sphingolipids are found in both plants and animals as a component of cellular and subcellular membranes. Ceramides may naturally occur in a glycosylated form or non glycosylated form, and may be isolated from either plant or animal tissues. Glycosylated ceramides have been reported to be non-toxic, moisturizing agents that also have anti-radical activity and an anti-elastase effect. (Bizot-Foulon V. et al., Int. J. Cosmetic Science 11, 255–264, 1995). In plants, ceramides are most commonly derived from wheat, rice, soya, millet and spinach. In the accompanying examples, commercially available glycosylated ceramides from wheat have been utilized where the aliphatic backbone has between 15 and 20 carbons. However, it is also within the scope of the invention to utilize polar lipids having a aliphatic backbone of 10–25 carbons. Plant polar lipids that are enriched in glycosyl ceramides may be purified according to the methods disclosed in FR-A-9106336; U.S. Pat. No. 5,466,782; and WO-A-92/21321. Commercial sources include Laboratoires Serobiologiques, France; and Les Colorants Wackherr, France.

The chemical structure of glycosylated ceramide includes a phytosphingosine backbone with a fatty acid attached by a carboxy amide bond to the aliphatic backbone, the backbone terminating in at least one saccharide for example, glucose via a glycosidic bond.

In embodiments of the invention, prolamine-plant polar lipid compositions have been formulated in a topical gel, patch or film so as to be suitable for delivering active agents either topically or systemically to the selected site. The selected site may include but not be limited to the skin or any of vaginal, rectal, nasal, buccal and ocular mucosa. Examples of topical applications using the inventive composition include cosmetically active agents exemplified by agents for improving skin appearance, topically active agents for treating dermal and nail diseases; agents for anti-hyperpigmentation, anti-blotching, anti-aging, eye contour, slimming, anti-cellulite, soothing/sunburn anti-irritating, skin firming and lifting, anti-elastase and anti-collagenase agents, free radical scavengers, seboregulators, hydratives, and AHA (α-hydroxy acids) specific products, and agents that generally act in protecting skin, healing skin, healing wounds and hemostasis Further examples of active agents for systemic or topical application according to embodiments of the invention include any of a variety of hydrophilic and hydrophobic agents of any therapeutic category such as antimicrobials including penicillin, tetracycline, erythromycin; anti-inflammatory agents such as salicylates, indole derivatives; hemostatic agents such as negatively charged phospolipids, particulate substances (kaolin); skin growth agents such as collagenase inhibitors, anti-acne agents including salicylic acid, benzoyl peroxide, and retinoic acid; local and systemic pain relievers such as procaine, lidocaine, xylocaine; sympathomimetic drugs such as epinephrine, amphetamine; antiparasitic agents such as metronidazole, fenthion, cythioate; cardiovascular agents such as nitroglycerine and nitrate compounds; hypoglycemic drugs such as insulin and insulin derivatives; nutritional agents such as vitamins, essential amino acids, essential fats; agents for smoking cessation such as nicotine; anti-arthritis agents; buccally active agents, such as those applied for pre- and post-dental operations, dental hygiene, mouth hygiene such as breathe refreshment and for systemic treatment of various diseases through the mouth mucosa, including morphine, meperidine, and keratolytic agent; wound healing agents; antipyretics; and anti-inflammatory agents including salicylates, indole derivatives; antispasmodics such as scopolamine, atropin; and hormonal agents such as cortisone, calcitonin.

The inventive composition including active agents selected from above can be used for skin protection and renewal, wound healing and hemostasis. In particular, wound healing agents include povidone-iodide, hyaluronic acid and its derivatives, Mastichinum oil from *Pistachia lentiscus* var. Chios, Greece, and any other compound known in the art and considered efficient for the treatment of conditions mentioned above.

The formation of the composition includes mixing proteins and plant polar lipids in a substantially homogeneous dispersion to provide a stable mixture with a characteristic three dimensional structure having properties that are suited for a wide range of medical applications. While not intended to be limited by theory, it is here suggested that the gliadin and ceramide interact to form a molecular lattice that results from non-covalent cross links and has the physical appearance of a gel or film. It is here suggested that the polyalcohol provides a hydroxyl rich environment to the gliadin-ceramide dispersion that has the effect of stabilizing the lattice and maintaining plasticity of the film in both dry and moist conditions. It is here suggested that plasticizers such as polyalcohol also improve the adhesiveness of the film formed from gliadin-ceramide gels. In examples of the invention, polyalcohol have been used at a concentration of about 12% on a wet basis (including the weight of hydroethanol) or 23% on a dry basis (excluding the weight of hydroethanol (Example 1) (about 4% glycerol and 8.5% sorbitol) whereas in example 11, polyalcohol represent about 65% of the gel on a dry basis. Indeed, polyalcohol may be utilized up to a concentration of 80% in the gel or film on a dry basis. The inventive composition provides an adhesive non-animal protein gel that can be formed into a film and is capable of remaining intact in both a moist environment and a dry environment for extended periods of time exceeding several hours. The lack of irritability and immunogenicity that is a property of the composition, enables the composition to be used for extended periods in contact with the skin. Films or patches formed from the composition need not be size limited other than by the size of the target site.

The composition may be applied effectively to wounds to promote healing. The composition permits the wound to remain hydrated. The composition forms a protective barrier against infection, and the composition is sufficiently porous to permit oxygen to access the wound. In addition the film is adhesive so that it remains in place for adequate periods of time and it is biodegradable so that it is not necessary to aggravate the wound by peeling off a non-biodegradable adhesive layer. The composition in the form of a film, provides a substrate to which therapeutic agents may be absorbed. This film may be folded and placed into an oral drug capsule, or formed into a patch for transdermal or topical delivery. FIGS. 1–7 show the some of the various types of patch in which the composition may be used.

In a preferred embodiment of the invention, the composition may be formed in a two step process. The first step is the formation of a gel containing the prolamine and plant polar lipid in a solvent with the optional presence of an active agent. The second step is to form the stable thin film or layer in which the solvent has been evaporated off so that the prolamine and plant polar lipid together with the optional active agent remains.

In an embodiment of the invention, a gel is formed by firstly adding prolamine to a hydro-alcoholic solution such as hydroethanol that has been heated to 40–50° C., more preferably 42 to 48° C. and vigorously stirred until a homogeneous dispersion is obtained; and then plant polar lipid and other ingredients including polyalcohol and active agent may be added. The mixture is vigorously stirred for a further 20 to 40 minutes at 42 to 48° C. after which time the dispersion is allowed to cool to ambient temperature, under gentle stirring (Example 1). Alternatively, in other embodiments, the reverse may be carried out with the prolamine being added to a solution of plant polar lipid. In further embodiments of the invention, the powder form of prolamine and lipids may be dissolved together in a hydroalcoholic solution to form a homogeneous dispersion; or a solution of prolamine and a solution of polar fatty acids may be mixed to form the dispersion. The proportions of the different components are exemplified in Example 1. The relative proportions of the prolamine to the plant polar lipids may vary substantially although, generally there is substantially more prolamine than polar plant lipids in the dispersion. An example of the range of concentrations includes a percentage weight of the total for each reagent in the ranges as given prolamine from 15 to 50% w/w, more particularly 20–40%; plant polar lipids: from 0.1 to 5% w/w; and hydro-alcoholic solution having a concentration of 35 to 80% alcohol/water such that the total is 100%. In a further embodiment of the invention, gliadin may be used having a concentration of about 31% w/w; wheat polar lipids of about 1.3% w/w and hydro-ethanolic solution (50%) to a total of 100%. The plant polar lipid may include at least 50% or greater than 50% of ceramide or a glycosyl ceramide.

In certain circumstances, it is desirable to incorporate a plasticizer in the gel so that the viscoelastic properties of the prolamines are improved. Examples of plasticizers include polyalcohol, more specifically natural polyalcohol such as glycerol and sorbitol. In Example 11, plasticizers formed as much as 65% of the dry weight of the gel. In Example 1, a homogeneous dispersion was formed from prolamine in the range of 20–40%; ceramide in the range of 1–2%; glycerol in the range of 2.5–5%; and sorbitol in the range of 6–9% and hydroalcoholic solution at 35–80% alcohol/water forming the remaining percentage to 100%.

Additional compounds including solvents, anti-oxidants, plasticizers, solubilizers, skin permeation enhancers, moisturizers, and preservatives may be added to the gel as appropriate. Selected solvents and solubilizers may be added so as to improve the solubility of ingredients, especially of the active agent. Skin permeation enhancers may be added to enhance the permeation of active agents through the skin and plasticizers have utility to enhance the flexibility of the film. In a preferred embodiment, plasticizers including natural polyalcohols enhance both the flexibility and the adhesiveness of the film. Furthermore, it is desirable to include an anti-oxidant in the patch such as vitamin E. Vitamin E was included in all the examples provided herein. Additional anti-oxidants such as vitamin C may be used to prevent any oxidation of active agents or to act as active substances themselves. Moisturizers could be added to provide an enhanced moisturizing effect while preservatives inhibit the growth of microbes in the patch. Examples 3–11 describe formulations of active agents in the prolamine plant polar lipid gels.

Figure 7A:
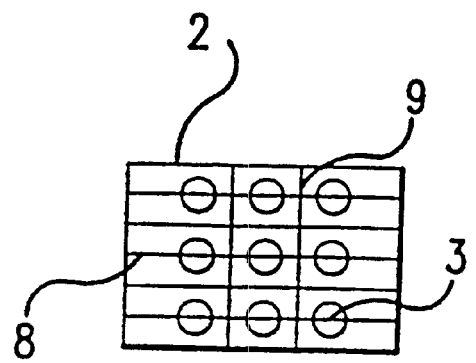
FIGS. 7(a) and (b) shows a set of circular patches in a format that is suitable for prolonged use by the patient. 7(a) shows the perforation lines (9) engraved in the middle of the device space while the scoring lines (8) are engraved horizontally. A rigid card forms the release liner, the gliadin and ceramide dispersion forms the adhesive matrix and the backing layer is formed from a flexible material. A treatment regimen might include the use in tandem of all patches. In (b) is shown a set of circular patches in which the release liner is gravure coated with a synthetic adhesive layer of DuroTak 72-8661 (4b).

Once a gel has been formed, this gel may be used for preparing a film or a patch (see Example 2). For forming a patch, it is desirable to caste the gel. In a preferred embodiment, the casting occurs on a non siliconized side of a polystyrene film and then the system is laminated on a siliconized polyester layer, previously coated with a thin layer of an acrylic adhesive. An embodiment of a patch composition is shown in FIG. 1 and FIG. 7. The prolamine-plant polar lipid film (1) is placed between a support surface such as a backing film (2) and optionally a release liner (3). The release liner is placed against the surface of the polymer layer, on the surface opposite to the backing film.

The backing film layer may be made of plastic, fabric, woven or non-woven materials that are porous or occlusive. The backing film can be made of any suitable material known in the art such as paper; cellophane; plastic films such as polyethylene, polyester, polyurethane, polyvinyl chloride and polyamide; fabrics and metallic foils which are impermeable and non-reacting with the active substances present in the polymer layer. The backing film can be composite, transparent, opaque or fleshtoned, or aluminized, or a combination thereof with a a thickness ranging from 1 to 5 mils (1/1000 of an inch) (about 25 to 130 μm) and can be formed from any of CoTran™ 9720 (3M), Saranex® (Dow Chemicals), Multilam fleshtoned polyester film 1009 (3M) or any other material recognized in the art as having the desirable properties. Preferably, the backing film is always breathable for those applications including skin protection and healing, wound healing and hemostasis.

Figure 2:
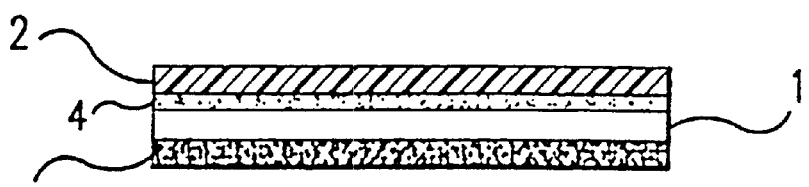
FIG. 2 shows a four layered patch where the backing film (2) may be initially laminated with a thin adhesive layer (4) upon which the composition is cast.
Figure 3:
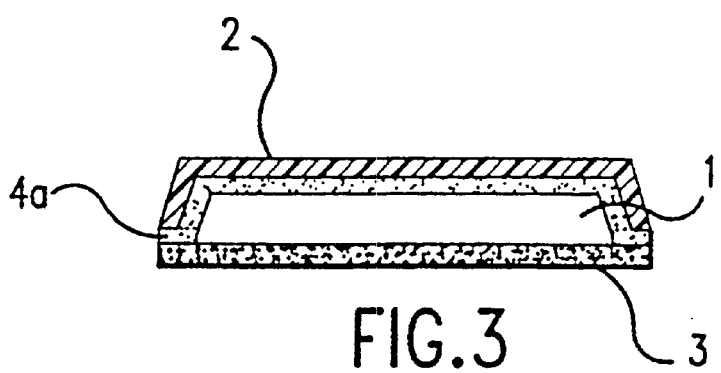
FIG. 3 shows a patch on which is further located, a peripheral adhesive layer (4a).
Figure 4:
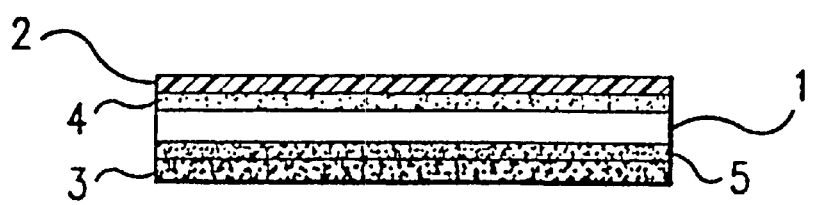
FIG. 4 shows a patch in which the polymer matrix is sandwiched between two layers of synthetic adhesive (5).
Figure 5:
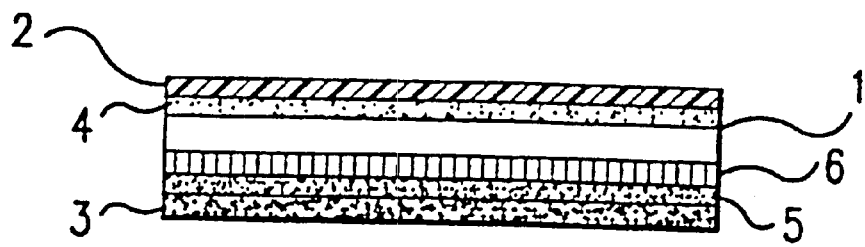
FIG. 5 shows a patch on which a porous membrane (6) is placed between the polymer matrix and the adhesive layer adjacent to the release liner.

The backing film (2) might be initially laminated with a thin synthetic adhesive layer (4), placed on the backing layer as presented in FIG. 2, which facilitates the casting of the gliadin-ceramide polymer layer but retains a surface for contact with a body surface such as skin. Similarly, the casting of a polymer layer can be achieved through a peripheral adhesive 4a as shown in FIG. 3. In this circumstance, the adhesive layer extends beyond the surface of the backing layer so that when the patch is applied to the body surface, some of the adhesive layer is in direct contact with the body surface. In FIG. 4, the dispersion is sandwiched between two adhesive layers so that the adhesive layer (5) is in full contact with the body surface once the release liner has been removed. In FIG. 5, the adhesive layer is in direct contact with the body surface after the release liner 3 is stripped off and is adjacent to a thin layer of a porous membrane (6) which in turn is adjacent to the gliadin/ceramide. The gliadin/ceramide dispersion is sandwiched between the release liner (3) and the porous membrane (6).

Figure 6:
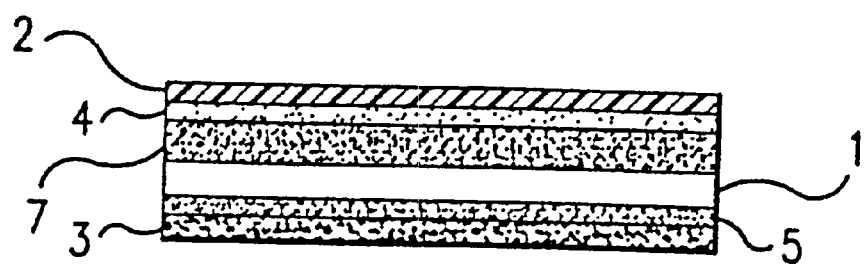
FIG. 6 shows a patch containing different concentrations of active agent acting as a gradient system for optimizing the efficacy of the patch. (7) is a polymeric layer that contains an increased amount of active compound compared with (1)

In another embodiment of the patch composition, a multi-layer gliadin/polar lipid dispersion is provided having for example, separate layers (7) containing increasing amounts of active agents in a gradient system for optimizing the efficacy of the patch, where layer 1 contains the lowest concentration of active agent and layer 7, the highest concentration of active agent as illustrated in FIG. 6.

The release liner can be made of materials impermeable to any substance present in the polymer layer and can be made of materials such as polyvinyl chloride, polyester, polyvinylidene chloride, polystyrene, polyethylene, paper etc. coated or not with an adhesive or a membrane.

Preferably the release liner is made of a natural high impact polystyrene film (grade code: 10106) or a siliconized polyester film, (both available from REXAM Release). The thickness of the release liner usually ranges from 3 to 10 mils (about 76 to 250 μm).

The membranes used for coating the release liner laminated with a thin layer of synthetic adhesive may be microporous or semipermeable. These membranes can be made of microporous polyethylene film or ethylene vinyl acetate film. Preferably, the membranes are made of CoTran® 9711 and CoTran® 9702 sold by 3M (USA).

The prolamine-plant polar lipid polymer may be used for topical or transdermal drug delivery including dermal, transdermal, mucosal (including vaginal and rectal), buccal or transmucosal administration. The film or patch formed from the prolamine-plant polar lipid dispersion can be produced with ease and reproducibility and is stable for the time period necessary for administration of the active agent. Furthermore, the film or patch is safe for humans (Examples 12 and 13). It may be made in a variety of forms, shapes, sizes and thicknesses dependent on the skin/mucosal site to be applied to and the type of treatment to be used. The prolamine-plant polar lipid composition may also be used to protect wounds from loss of moisture and from infection and to stimulate healing in wounds. The prolamine-plant polar lipid composition may also be used to control bleeding and to maintain hemostasis.

The plant-prolamine composition may be administered in the form of a film by using an aerosol applicator where the film is formed on the skin as the hydroalcoholic solvent evaporates or alternatively, the film may be precast prior to its application. The adhesive properties of the prolamine-plant polar lipid dispersion arise when the surface to which the dispersion is to be applied, is moist. This may be achieved by hydrating the body surface with physiological saline or water (grade for injection). In some circumstances, the body surface is already moist such as occurs for wounds and for mucosa so that there is no need for further hydration.

The adhesiveness of the gliadin film may be enhanced by increasing the total amount of polyalcohol used for the preparation of gliadin ceramide gel. For this purpose, the concentration of polyalcohol in the gel may range, on a dry basis, from 10 to 80% or preferably from 20 to 70% of the total amount of the ingredients present in the gel.

In the present invention, the polymer carrier system in the form of a film or patch may be sterilized using gamma radiation techniques as described by US and European Pharmacopoeias. In another embodiment of the present invention, the polymer film can be folded and encapsulated in a hard capsule for oral controlled delivery of drugs, The invention is merely illustrated by the following examples which should not be considered to limit the scope of the invention, as these examples and other equivalents thereof will become apparent to those skilled in prior art in the light of the present disclosure and drawings. The scope of the invention is defined by the appended claims.

EXAMPLES

Example 1

Preparation of a Prolamine-plant Polar Lipid Gel 272 g of gliadin powder and 12 g of ceramide powder was added to 604 g of a hydroethanolic solution (50% ethanol in water) to form a dispersion. 33 g of glycerol (purity 99%) and 78 g of sorbitol (purity 70%) were added to the dispersion. The weight percentage of polyalcohol is about 12% wet basis and about 23% on dry basis (excluding the weight of hydroethanol) The mixture was placed in a water bath at 46° C. (a temperature of 42–48° C. is suited for this purpose) and vigorously stirred until a substantially homogeneous dispersion was obtained. The dispersion was then allowed to cool at ambient temperature under gentle stirring to form a gel with a viscosity of 700–1500 gm/cm.sec (cPoise). This gel could be formed into a film by spreading or spraying the gel on a surface to permit it to dry.

Example 2

A Topical Patch Formed from Gliadin-Ceramide Containing an Active Agent

The preparation of a patch containing an active agent is as follows.

Step (1) The active agents together with the components listed below in Table 1, were incorporated into a gel formed from the homogeneous dispersion of gliadin/ceramide as described in Example 1.

Step (2) A first patch was manufactured that consisted of a backing film, a synthetic adhesive and a release liner. The adhesive film was cast onto the backing film using a coating device (square tool Multi-clearance Applicator, (BYK Gardner, USA)) with a 5 mil (about 130 µm) casting gap. A layer of a synthetic adhesive such as Duro-Tak 87-2353 was coated onto a siliconized polyester film and dried in an oven at 70–75° C. for 15–18 minutes. A low density polyethylene film was then laminated on the synthetic adhesive film.

Step (3) A second patch was manufactured consisting of a release liner and layer of gliadin/ceramide dispersion including the active agents and other compositions listed below in Table 1. Using a 5 mil (about 130 µm) casting gap, a layer of gliadin/ceramide dispersion, as prepared in Example 1, was coated onto the non-siliconized side of a polystyrene film and dried in the oven at 60–62° C. for 10–12 minutes using the Multiclearance Applicator.

Step (4) The release liner on the first patch is discarded and the exposed adhesive layer is brought into contact with the gliadin/ceramide dispersion of the second patch to form the laminate for use on the patient. The multi-layer laminate was then cut in one of two ways:

(a) the release liner was passed through a Flexomaster 1B (Allied Gear-Netherlands) and circular patches of 0.5" (about 1.3 cm) diameter were cut, leaving the release liner intact (see FIG. 7). As shown in FIG. 7, scoring (8) and perforation (9) lines were simultaneously engraved at a perpendicular to each other. The perforations separated individual patches.

Figure 7B:
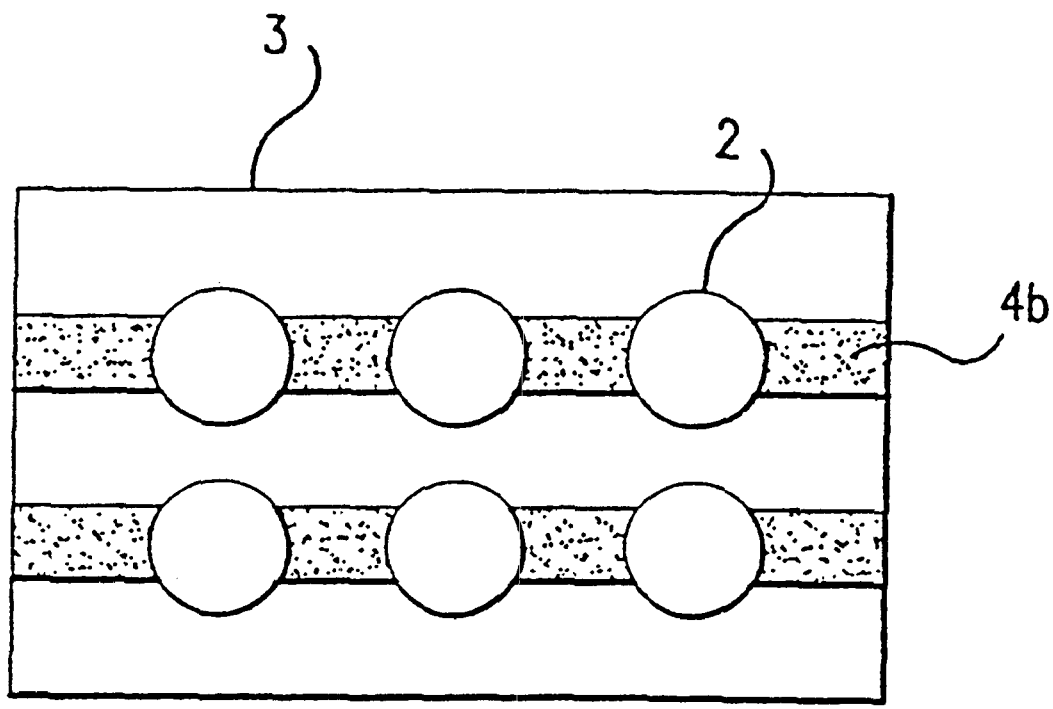
Figure 8:
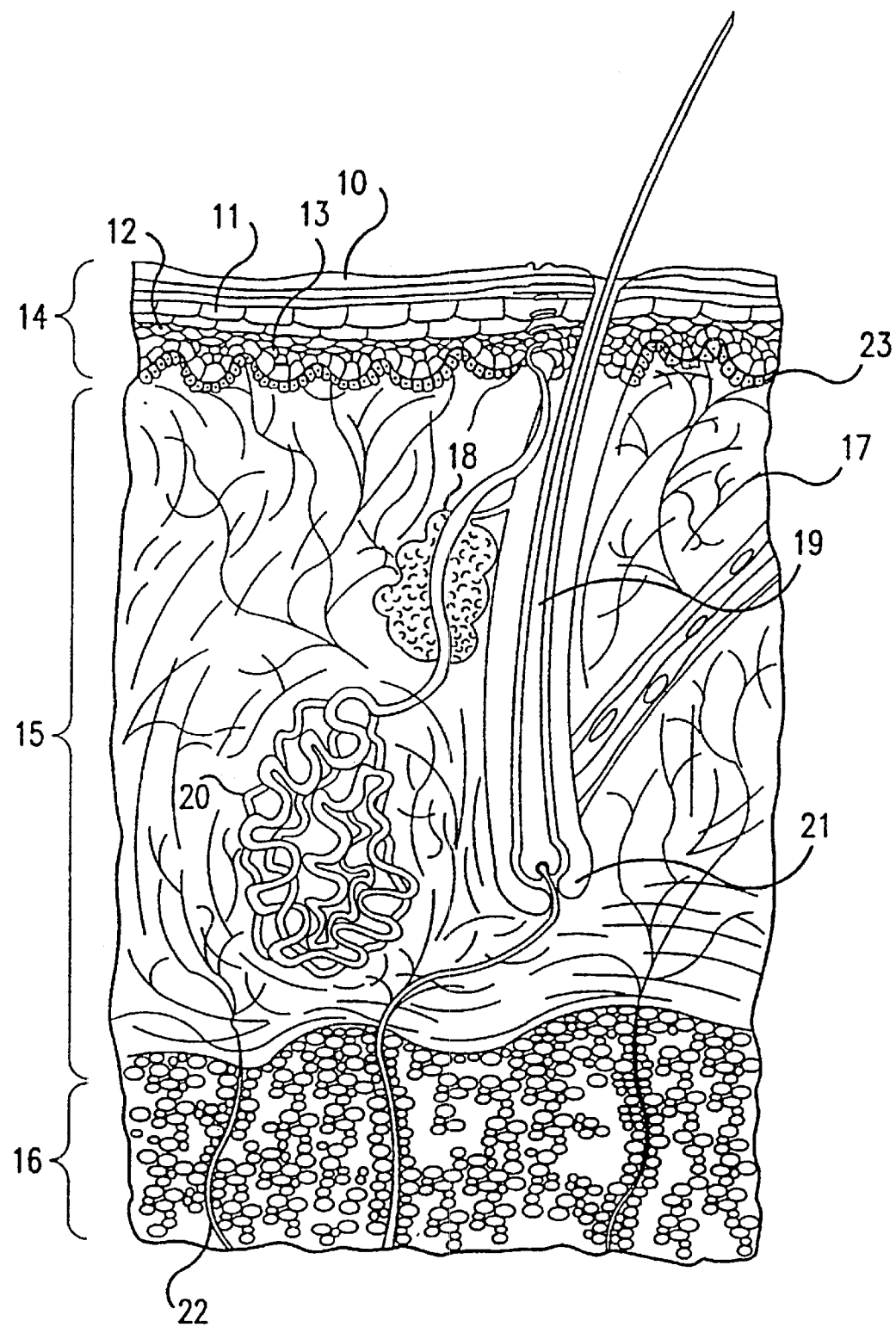
FIG. 8 shows a diagrammatic representation of a skin cross section to illustrate the extent of penetration of the active agent to the basal layer in a topical administration versus a penetration to the capillaries in the dermis of an agent in a systemic administration. (10) stratum corneum, (11) Stratum Lucidum, (12) Stratum Spinosum, (13) Stratum Germinativum, (14) epidermis (15) dermis (16) hypodermis (17) capillary network (18) sebaceous gland (19) hair shaft (20) apocrine sweat gland (21) hair follicle (22) blood vessel (23) basal layer.

(b) the release liner was gravure coated with a synthetic adhesive layer of DuroTak 72-8661 (4B) as shown in FIG. 7b.

Example 3

A Topical Patch Formed from Gliadin-Ceramide Containing an Anti-acne Agent

The anti-acne patch was formed using the gel of Example 1 and the method of forming a patch disclosed in Example 2.

TABLE 1

Composition of the mixture

| COMPONENT | QUANTITY % w/w |
|---|---|
| Gel of Example 1 | 89.08 |
| Anti-acne agent* | 10.00 |
| Phenonip ® ** | 0.45 |
| Potassium Sorbate*** | 0.05 |
| DL-α-Tocopherol | 0.42 |

*The anti-acne agent is any agent known in the art for treating acne
**Phenonip ® Nipa Lab, is a mixture of phenoxyethanol, methylparaben, ethylparaben, propylparaben and butylparaben and acts as a preservative
***Potassium sorbate is a multifunctional agent capable of action as a preservative

Example 4

Preparation of a Gliadin-Ceramide Patch Containing a Skin Whitening Agent

The skin whitening patch was formed using the gel of Example 1 and the method of forming a patch disclosed in Example 2.

TABLE 2

Composition of the mixture

| COMPONENT | QUANTITY % w/w (on a dry basis) | |
|---|---|---|
| | Formulation A | Formulation B |
| Gel of Example 1 | 83.72 | 87.00 |
| Etioline[1] ® | | 5.00 |
| Gatuline ® Whitening[2] | 9.70 | 5.00 |
| Ascorbyl palmitate | | 2.00 |
| Arlacel 80[3] | 5.80 | |
| Dl-α-Tocopherol | 0.78 | 1.00 |

[1]Etioline ® Sederma, France is an African plant extract (Matricarpe of Spermacocea genus), which can inhibit tyrosinase, an enzyme responsible for melanin synthesis.
[2]Gatuline ® whitening, Gattefosse, France obtained by fermentation of kojic acid and lactic acid, is a tyrosinase inhibitor.
[3]Arlacel 80 ® ICI USA is a multifunctional agent that is useful as a solubilizer, plasticizer and emulsifier.

Example 5

Preparation of a Gliadin-Ceramide Patch Containing a Local Anesthetic

The anesthetic patch was formed using the gel of Example 1 and the method of forming a patch disclosed in Example 2. Where this patch is used for dental purposes, an antiseptic is introduced into the gel in addition to the anesthetic prior to forming the patch.

TABLE 3

Composition of a gliadin mixture

| COMPONENT | QUANTITY % w/w (on a dry basis) | | | | | | |
|---|---|---|---|---|---|---|---|
| | A | B | C | D | E. | G | G |
| Gel of Example 1 | 88.68 | 94.34 | 91.51 | 98.80 | 96.3 | 94.7 | 89.7 |
| Lidocaine HCl | 11.31 | 5.65 | 8.49 | 1.00 | 2.7 | 5.0 | 10.0 |
| Chlorohexidine digluconate | | | | 0.20 | 1.0 | 0.3 | 0.3 |

Example 6

Preparation of a Gliadin-Ceramide Patch Containing Skin Firming Agents

The skin firming patch was formed using the gel of Example 1 and the method of forming a patch disclosed in Example 2.

TABLE 4

| COMPONENT | QUANTITY % w/w (on a dry basis) | | | |
|---|---|---|---|---|
| | A | B | C | D |
| Gel of Example 1 | 89.09 | 87.09 | 86.92 | 81.09 |
| Firming/lifting agent* (Gatuline ®) | 3.00 | 5.00 | 3.00 | 8.00 |
| Retinyl palmitate | 2.00 | 2.00 | 2.00 | 2.00 |
| Gatuline ® RC** | 5.00 | 5.00 | 5.00 | 8.00 |

TABLE 4-continued

| COMPONENT | QUANTITY % w/w (on a dry basis) | | | |
|---|---|---|---|---|
|  | A | B | C | D |
| DL-α-Tocopherol | 0.17 | 0.17 | 2.34 | 0.17 |
| Transcutol ® *** | 0.74 | 0.74 | 0.74 | 0.74 |

*Gatuline firming/lifting is a plant extract containing flavanoids, tannins and a protein fraction having similar properties to bovine serum albumin.
**Gatuline RC is a beech tree buds extract containing flavanoids, peptides such as phytostimulins and others.
***Transcutol ® Gattefosse, France is a glycol

Example 7

Preparation of a Gliadin-Ceramide Patch Containing a Keratolytic Agent

A patch containing a keratolytic agent was formed using the gel of Example 1 and the method of forming a patch disclosed in Example 2.

TABLE 5

| COMPONENT | QUANTITY % w/w |
|---|---|
| Gel of Example 1 | 99.50 |
| Salicylic acid | 0.50 |

Example 8

Preparation of a Gliadin-Ceramide Patch for Skin Renewal

A patch for skin renewal was formed according to Example 1 and Example 2.

TABLE 6

| COMPONENT | QUANTITY % w/w |
|---|---|
| Gel of Example 1 | 98.58 |
| Collagenase inhibitor | 0.20 |
| Phenonip ® | 0.75 |
| Potassium Sorbate | 0.05 |
| DL-α-Tocopherol | 0.42 |

Example 9

Preparation of a Gliadin Ceramide Patch for Wound Healing

A patch was formed according to Example 1 and Example 2. Alternatively, the gel of Example 1 was sprayed onto the wound and permitting to dry so as to form a thin film.

TABLE 7

| COMPONENT | QUANTITY % w/w |
|---|---|
| Gel of Example 1 | 92.58 |
| Mastichinum oil | 5.00 |
| α-Bisabolol | 1.20 |
| Phenonip ® | 0.75 |

TABLE 7-continued

| COMPONENT | QUANTITY % w/w |
|---|---|
| Potassium Sorbate | 0.05 |
| DL-α-Tocopherol | 0.42 |

Example 10

Preparation of a Gliadin Ceramide Patch Containing an Anti-microbial Agent

A patch was formed according to Example 1 and Example 2 or alternatively a gel according to Example 1 was sprayed onto the wound permitting it to dry to form a thin film.

TABLE 8

| COMPONENT | QUANTITY % w/w |
|---|---|
| Gel of Example 1 | 95.00 |
| Povidone iodide | 5.00 |

Example 11

Preparation of a Gliadin-Ceramide Patch Containing Multifunctional Agents for Acute Refreshment of the Skin A patch was formed according to Example 1 and Example 2 or alternatively a gel according to Example 1 was sprayed onto the skin surface permitting it to dry to form a thin film.

Reagents were included in the formulation as indicated below to achieve nutrition of the skin, enhanced elasticity of the skin, improved microcirculation, removal of wrinkles and anti-irritant activity.

TABLE 9

| COMPONENT | QUANTITY % w/w | |
|---|---|---|
|  | A | B |
| Gel of Example 1[1] | 82.15 | 87.65 |
| Aminoacid mixture[2] | 4.00 | 4.00 |
| Sodium hyaluronate | 1.00 | 1.00 |
| Caffeine (for microcirculation) | 1.00 | 1.00 |
| Zn gluconate | 0.10 | 0.10 |
| Mg gluconate | 0.10 | 0.10 |
| Mn gluconate | 0.10 | 0.10 |
| α-Bisabolol | 1.50 | 1.50 |
| Retinyl palmitate | 0.50 | 0.50 |
| Ascorbyl palmitate | 1.00 | 1.00 |
| Vitamin F | 0.50 | 0.50 |
| G.D. 700[3] | 0.30 | 0.30 |
| BHT[4] | 0.05 | 0.05 |
| D-Panthenol | 0.50 | 0.50 |
| Vitamin K | 1.00 | 1.00 |
| Menthol | 0.50 |  |
| Hydraprotectol[5] | 5.00 |  |
| Glycyrrhetinic acid | 0.50 | 0.50 |
| EDTA 2Na[6] | 0.2 | 0.20 |

[1]Glycols represent 64.81% of the total amount on a dry basis where gliadin is present at 272 g, and ceramide at 12 g to which 604 g hydroethanolic solution is added. 0.42% tocopherol is included in the homogeneous dispersion
[2]The amino acid mixture includes glycine, proline, lysine and leucine.

TABLE 9-continued

| | QUANTITY % w/w | |
|---|---|---|
| COMPONENT | A | B |

[3]G.D. 700 is preservative consisting of phenoxethanol and methyl-, butyl isbutyl-, propyl-, ethylparaben. (surfactants)
[4]BHT (butylated hydroxy toluene) is an antioxidant.
[5]Hydraprotectol is a long lasting hydrating agent consisting of water, glyceryl polymethacrylate, glycerin, glycoproteins, yeast, extract and D291 aleuretic acid
[6]FDTA 2Na is the disodium salt of ethylenediaminetetraacetic acid.

Example 12

Gliadin-Ceramide Patches are Safe as Delivery Devices for Active Agents Locally and Systemically A gliadin ceramide gel was formed according to Example 1 and further contained (a) Vitamin E (0.78% w/w di-α-tocopherol) (b) vitamin E and 10% providone iodide. Betadine® ointment (Mundipharma, Bermuda) was used as a control and showed zero irritation in the test.

The irritation potential for the gliadin ceramide patch was determined in a Primary Dermal Irritation Study, in compliance with the FDA Requirements per 21 CFR 58 to identify the potential irritation on rabbit skin when exposed to the test material.

The fur of six healthy New Zealand rabbits was clipped as close to the skin as possible at the test sites twenty-four hours prior to the application of patch and ointment samples. Duplicate samples were applied to both intact and abraded skin. The skin was exposed to the samples for a period of twenty-four hours and examinations of the animals for signs of erythema, edema and any lesions or other toxic effects were made at thirty to sixty minutes after patch removal and, then, at seventy-two hours. The Primary Irritation Score as estimated was O for both patches (patch with vitamin E and patch with povidone iodine). The results showed that neither of the patches produced any sign of erythema or edema at the two test sites. In addition, no other toxic effects were observed during the study. Consequently it was concluded that Prolamine-plant polar lipid patches are not a primary dermal irritant as defined in 16 CFR 1500.3 (c) (4).

Example 13

Repetitive Application Patch Test

The irritation potential and cutaneous tolerance of the prolamine-plant polar lipid patches was also determined on human skin. Because of the lower sensitivity of human skin to irritants, versus animal model, testing in humans is generally performed by repetitive application patch testing (Phillips, L et al Toxical Appl. Pharmacol. 21, 369–382, 1972 and Method of testing primary irritant substances, United States Code of Federal Regulations 16 CFR 1500 41, 1979). This method is also in accordance with the International Prescription for Cosmetics Safety (Cosmetic safety. A Primer for Cosmetic Scientists. Editor James Whittan Markel Dekker Inc. New York and Basel 1987). Skin Grading was performed according to erythema, oedema and exudation, as described below in Table 10.

The test involves 20 volunteers, male or female (20–60 years old), whose upper back are free from any skin problems. None of the subjects was under treatment local or systemic which might interfere with the study aims. The test patch was formed according to Example 1 and vitamin E was added to the gel prior to forming a film. The test patch was backed with tape and placed on the upper back of the subjects for 24 hours and, then, removed. One hour after removal of the patch test the skin site was wiped with moist cotton wool ball and graded. 24 hours later the patches were applied again on the same place. According to this method the patch tests were performed for 20 days (10 applications) in 20 volunteers with sensitive skin. Nineteen volunteers scored 0 and 1 volunteer scored 1. The results of this study showed that the gliadin ceramide patch is safe and non irritating for humans.

TABLE 10

Classification - scores

| Scores | Erythema | Edema | Exudation or Surface Encrustation |
|---|---|---|---|
| 0 | No erythema | No edema | No effects |
| 1 | Very slight erythema | Very slight edema | Up to one half of the treated area affected |
| 2 | Well defined erythema | Slight edema | More than one half of the treated area affected |
| 3 | Moderate to severe erythema | Moderate edema | |
| 4 | Severe erythema | Severe edema | |

What is claimed is:

1. A composition, comprising: a mixture of a prolamine, a plant polar lipid, at least one polyalcohol in a hydro-alcoholic solution, and an active agent, wherein the composition forms a substantially homogeneous dispersion with skin adhesive properties; wherein the dispersion forms a film and wherein the film contains a gradient of concentrations of the active agent.

2. A composition according to claim 1, wherein the prolamine is a cereal prolamine.

3. A composition according to claim 2, wherein the cereal prolamine is gliadin.

4. A composition according to claim 1, wherein the plant polar lipid is isolated from a cereal.

5. A composition according to claim 1, wherein the hydro-alcoholic solution is hydro-ethanol.

6. A composition according to claim 4, wherein the plant polar lipid is a preparation that includes a ceramide or a glycosylceramide at a concentration greater than 50%.

7. A composition according to claim 1, wherein the prolamine has a w/w in the range of 20–40%, the plant polar lipids have a w/w in the range 0.1%–5%.

8. A composition according to claim 1, further comprising a plasticizing agent.

9. A composition according to claim 8, wherein the polyalcohol comprises a concentration of glycerol or a concentration of sorbitol.

10. A composition according to claim 9, wherein the concentration of polyalcohol is in the range of 2.5%–80% dry weight.

11. A composition according to claim 1, wherein the active agent is a therapeutic agent.

12. A composition according to claim 1, wherein the active agent is a cosmetic agent.

13. A composition according to claim 1, wherein the film is rolled into a compact form.

14. A composition according to claim 1, wherein the dispersion is in a form suited for adhering at a site selected from oral, buccal, rectal, vaginal and topical sites.

15. A composition according to claim 8, wherein the film forms a protective barrier for underlying tissue, on a wound surface.

16. A composition according to claim 15, wherein the protective barrier retains a therapeutic agent for promoting wound healing.

17. A composition according to claim 1, wherein the dispersion has hemostatic properties.

18. A composition according to claim 15, wherein the wound is a burn.

19. A composition according to claim 11, wherein the active agent is selected from the group comprising: local and systemic pain relievers, anti-arthritis agents; buccally active agents, agents for enhancing dental hygiene, agents for enhancing mouth hygiene, antimicrobials agents, anesthetic agents, keratolytic agent; wound healing agents; antipyretics; anti-inflammatory agents, antispasmodic agents, sympathomimetic drugs, antiparasitic agents, hypoglycemic drugs, nutritional agents, cardiovascular agents, agents for smoking cessation, vitamins, hemostatic agents, skin growth agents.

20. A composition according to claim 12, wherein the active agent is selected from the group comprising: agents for improving skin appearance, topically active agents for treating dermal and nail diseases; anti-hyperpigmentation, anti-blotching, anti-aging, eye contour, slimming, anti-cellulite, soothing/sunburn anti-irritating, skin firming and lifting, anti-elastase and anti-collagenase agents, free radical scavengers, seboregulators, hydratives, and AHA ($\alpha$-hydroxy acids) specific products.

21. A composition according to claim 1, further comprising an oxidizing agent contained within the dispersion.

22. A composition according to claim 21, wherein the oxidizing agent is vitamin E.

* * * * *